United States Patent [19]
Eberle et al.

[11] Patent Number: 5,300,521
[45] Date of Patent: Apr. 5, 1994

[54] PYRAZOLES, FUNGICIDAL COMPOSITIONS AND USE

[75] Inventors: Martin Eberle, Allschwil; Fritz Schaub, Aesch, both of Switzerland

[73] Assignee: Sandoz Ltd., Basel, Switzerland

[21] Appl. No.: 116,234

[22] Filed: Sep. 1, 1993

Related U.S. Application Data

[63] Continuation of Ser. No. 60,769, May 10, 1993, abandoned.

[30] Foreign Application Priority Data

May 13, 1992 [GB] United Kingdom ............... 9210224
Mar. 2, 1993 [GB] United Kingdom ............... 9304198

[51] Int. Cl.$^5$ ............... A01N 43/56; A01N 43/78; C07D 231/12; C07D 417/06
[52] U.S. Cl. ............... 514/406; 514/341; 514/365; 514/367; 546/279; 548/170; 548/204; 548/365.7; 548/376.1
[58] Field of Search ............... 548/204, 365.7, 376.1; 514/365, 406

[56] References Cited

U.S. PATENT DOCUMENTS 5,128,350  7/1992  Oda et al. ............... 548/365.7

FOREIGN PATENT DOCUMENTS 178826  10/1985  European Pat. Off. .
348766   6/1989  European Pat. Off. .
378755  10/1989  European Pat. Off. .
433899  12/1990  European Pat. Off. .
471262   8/1991  European Pat. Off. .
483851  10/1991  European Pat. Off. .

Primary Examiner—Robert W. Ramsuer
Attorney, Agent, or Firm—Allen E. Norris; Lynn Marcus-Wyner

[57] ABSTRACT

The invention compounds of formula I

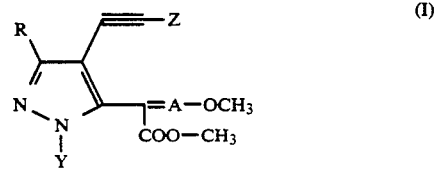

wherein
R is H, $C_{1-4}$alkyl; optionally substituted aryl or $CF_3$;
Y is $C_{1-4}$alkyl or optionally substituted aryl;
A is nitrogen or CH; and
Z is optionally substituted hydrocarbyl or optionally substituted heteroaryl;

the use of such compounds for the control of phytopathogens, compositions for facilitating such use, and the preparation of compounds of formula I.

8 Claims, No Drawings

PYRAZOLES, FUNGICIDAL COMPOSITIONS AND USE

This is a continuation of application Ser. No. 08/060,769, filed on May 10, 1993 now abandoned.

This invention relates to novel pyrazolyl acetic acid derivatives, the synthesis thereof and the use of said compounds for the control of phytopathogens.

α-(Pyrazol-5-yl)-β-methoxy acrylates substituted in the 4 positions of the pyrazole ring by certain arylmethoxy groups are known from EP-A-0433899. Said compounds have been proposed as agricultural/horticultural fungicides.

It has now been found that compounds of formula I

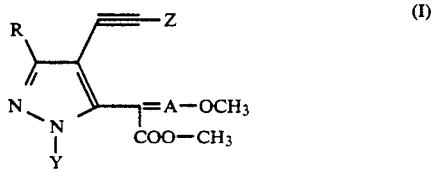

wherein
R is H, $C_{1-4}$alkyl; optionally substituted aryl or $CF_3$;
Y is $C_{1-4}$alkyl or optionally substituted aryl;
A is nitrogen or CH; and
Z is optionally substituted hydrocarbyl or optionally substituted heteroaryl;
are surprisingly effective against phytopathogens.

Where R and/or Y are optionally substituted aryl they are preferably optionally substituted phenyl. Where R and/or Y are substituted aryl, e.g. phenyl, they are preferably mono- to di-substituted. Preferably such substituents are selected from $C_{1-4}$alkyl, $C_{1-4}$alkoxy, $C_{1-4}$haloalkyl, $C_{1-4}$haloalkoxy and halogen.

R is preferably $CH_3$ of $CF_3$. Y is preferably $C_{1-4}$alkyl, especially $CH_3$.

The terms haloalkyl and haloalkoxy as used herein relate to alkyl and alkoxy substituted by one or more, e.g. one to three halogens; typical examples for these significances are $CF_3$ and $CF_3O$.

Where Z is optionally substituted hydrocarbyl, the hydrocarbyl may be aliphatic, aromatic or araliphatic. The aromatic moieties are however preferred.

Where it is an aliphatic hydrocarbyl it may be straight or branched or form a ring and is preferably selected from $C_{1-9}$ alkyl, $C_{3-8}$cycloalkyl and $C_{3-8}$cycloalkyl-$C_{1-4}$ alkyl.

Where Z is a substituted aliphatic hydrocarbyl, it may for example be substituted by halogen, phenoxy or phenoxy mono- or disubstituted by substituents selected from $C_{1-4}$alkyl, $C_{1-4}$alkoxy, $C_{1-4}$haloalkyl, $C_{1-4}$haloalkoxy and halogen. Preferred substituted aliphatic hydrocarbyl groups Z are haloalkyl, phenoxyalkyl and phenoxyalkyl mono- or disubstituted in the phenyl moiety. The alkyl moiety of such aliphatic hydrocarbyl groups has preferably 1 to 4 carbon atoms. Typical examples for such groups include unsubstituted or mono- or di-substituted phenoxy methyl.

Where Z is an aromatic hydrocarbyl, i.e. aryl, it is preferably phenyl.

Where Z is an araliphatic hydrocarbyl, i.e. aralkyl, it is preferably phenylalkyl, in particular phenyl-$C_{1-4}$alkyl such as phenyl-$C(CH_3)_2$.

Where Z is an heteroaryl, it is preferably a 5- or 6-membered ring having 1 or 2 heteroatoms in its ring selected from S and N, more preferably thienyl, pyridyl, thiazolyl and pyrimidinyl.

Where Z is a substituted aryl or substituted heteroaryl, it may for example bear one or more substituents X.

Where Z is substituted aralkyl it may be substituted in the aryl moiety and in the alkylene moiety. Where the alkylene moiety is substituted it is preferably monosubstituted by hydroxy or $C_{1-4}$alkoxy. Where the aryl moiety is substituted it bears conveniently one or more substituents X, especially one, two or three substituents X.

X is independently hydrogen; halogen; $C_1$–$C_{10}$ alkyl, $C_2$–$C_{11}$ alkenyl, $C_1$–$C_{10}$ alkoxy, $C_2$–$C_{11}$ alkenyloxy or $C_2$–$C_{11}$ alkynyloxy, each optionally substituted with one or more substituents selected from halogen, trifluoromethyl and $C_1$–$C_5$ alkoxy; or $C_6$–$C_{12}$ aryl, $C_6$–$C_{12}$ aryloxy, $C_2$–$C_{13}$ heteroaryl having 1-3 heteroatoms selected from oxygen, sulphur, and nitrogen, total number of atoms of said heteroaryl being 5-14, $C_2$–$C_{13}$ heteroaryloxy having 1-3 heteroatom(s) selected from oxygen, sulphur, and nitrogen, total number of atoms of said heteroaryloxy being 5-14, $C_7$–$C_{12}$ aralkyl or $C_7$–$C_{12}$ aralkyloxy optionally substituted with one or more substituents selected from halogen, trifluoromethyl, $C_1$–$C_5$ alkyl and $C_1$–$C_5$ alkoxy; or two Xs may be fused to form a bi- or tricyclic ring together with the aryl or heteroaryl to which they are attached.

In the definition of X the term $C_1$–$C_{10}$ alkyl includes, for example, methyl, ethyl, n-propyl, isopropyl, n-butyl, t-butyl, n-pentyl, isopentyl, t-pentyl, neopentyl, 1-methylbutyl, hexyl, heptyl, octyl, nonyl, decyl; the term $C_2$–$C_{11}$ alkenyl includes, for example, vinyl, allyl, 1-propenyl, 2-butenyl, 1,3-butadienyl, 2-pentenyl; the term $C_1$–$C_{10}$ alkoxy includes methoxy, ethoxy, propoxy, isopropoxy, n-butoxy; the term $C_2$–$C_{11}$ alkynyloxy includes, for example propargyloxy; the term $C_6$–$C_{12}$ aryl includes, for example, phenyl, tolyl, xylyl, naphthyl; the term $C_6$–$C_{12}$ aryloxy includes, for example, phenoxy, toryloxy, naphthyloxy; the term $C_2$–$C_{13}$ heteroaryl includes, for example, thiazolyl, benzothiazolyl, pyridyl; the term $C_2$–$C_{13}$ heteroaryloxy includes, for example, thiazolyloxy, benzothiazolyloxy, pyridyloxy; the term $C_7$–$C_{12}$ aralkyl includes, for example, benzyl, phenethyl; the term $C_7$–$C_{12}$ aralkyloxy includes, for example, benzyloxy, phenethyloxy.

X is preferably hydrogen; halogen; optionally substituted $C_1$–$C_4$ alkyl, $C_2$–$C_3$ alkyl, $C_1$–$C_3$ alkoxy, $C_2$–$C_3$ alkenyloxy, $C_2$–$C_3$ alkynyloxy, each optionally substituted with one or more substituents selected from halogen and trifluoromethyl; or phenyl, phenoxy, benzyl, benzyloxy, thiazolyl, thiazolyloxy, pyridyloxy, or benzothiazolyloxy, each optionally substituted with one or more substituents selected from halogen, trifluoromethyl, $C_1$–$C_4$ alkyl and $C_1$–$C_5$ alkoxy. More preferably, X is hydrogen, fluorine, chlorine, bromine, optionally substituted methyl, butyl, optionally substituted methoxy, optionally substituted ethoxy, optionally substituted propoxy, optionally substituted propenyloxy, propargyloxy, butyloxy, optionally substituted phenyl, optionally substituted phenoxy, optionally substituted benzyl, benzyloxy, thiazolyloxy, benzothiazolyloxy, optionally substituted pyridyloxy, or benzoyl. Preferred substituents for methyl, methoxy, ethoxy, propoxy and propenyloxy groups include fluorine and chlorine. Preferred substituents for phenyl, phenoxy, benzyl and pyridyloxy include methyl, butyl, methoxy, fluorine, chlorine and trifluoromethyl.

When an adjacent X forms a fused ring together with the benzene ring or thiazol ring to which they are attached, the fused ring may be preferably 2,3-dihydrobenzofuran, chroman, naphthalene, fluorene, anthraquinone, or benzo-1,3-dioxolane.

Therefore, preferred compounds are those of formula (I), as defined above, in which Z is thienyl or a group of formula G1 or G2:

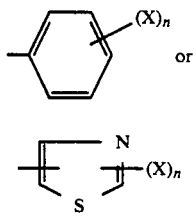

wherein X is independently hydrogen; halogen; $C_1$-$C_4$ alkyl, $C_2$-$C_3$ alkenyl, $C_1$-$C_3$ alkoxy, $C_2$-$C_3$ alkenyloxy or $C_2$-$C_3$ alkynyloxy, each optionally substituted with one or more substituents selected from halogen and trifluoromethyl; or phenyl, phenoxy, benzyl, benzyloxy, thiazolyl, thiazolyloxy, pyridyloxy or benzothiazolyloxy, each optionally substituted with one or more substituents selected from halogen, trifluoromethyl, $C_1$-$C_4$ alkyl and $C_1$-$C_4$ alkoxy; m is 1 or 2; and n is a integer of 1-5; or two Xs may form a fused ring together with the benzene ring to which they are attached, where the fused ring is selected from 2,3-dihydrobenzofuran, chroman, naphtalene, fluorene, anthraquinone or benzo-1,3-dioxolane.

Particularly preferred compound of the formula I are those wherein Z is G1 which comprises one or two substituents selected from the above group of X. These substituents are preferably in the 3- or 4-position of the phenyl ring. Examples for corresponding substituents Z are: chlorophenyl as 4-chlorophenyl, fluorophenyl as 4-fluorophenyl, methoxyphenyl as 4-methoxyphenyl, metylphenyl as 4-methylphenyl, trifluormethylphenyl as 3-trifluoromethylphenyl, dichlorophenyl as 3,4-dichlorophenyl or 2,5-dichlorophenyl, 3-chloro-4-methoxyphenyl or 3-chloro-4-methylphenyl.

Halo as used herein refers to fluoro, chloro, bromo and iodo unless otherwise noted preferably will be fluoro or chloro.

All the compounds of the invention are novel and can be prepared according to the general process described below.

The compounds of formula (I), contain at least one carbon-A double bond, and are sometimes obtained in the form of mixtures of geometric isomers. However, these mixtures can be separated into individual isomers, and this invention embraces such isomers, and mixtures thereof in all proportions, including those which consist substantially of the (Z)-isomer and those which consist substantially of the (E)-isomer. The individual isomers which result from the unsymmetrically substituted double bond, are identified by the commonly used terms "E" and "Z". These terms are defined according to the Cahn-Ingold-Prelog system which is fully described in the literature (see, for example, J. March, "Advanced Organic Chemistry", 3rd edition, Wiley-Interscience, page 109 et seq.).

Compounds of formula I are obtained by O-methylation of a compound of formula II

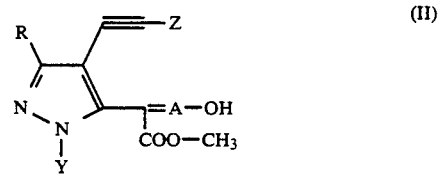

wherein A, R, Y and Z are as defined above.

The O-methylation can be carried out in a manner known per se for the preparation of 3-methoxyacrylates employing conventional methylation agents.

Examples of suitable methylation agents include methyl iodide and dimethyl sulphate.

The O-methylation is conveniently carried out in the presence of a base.

The reaction temperature will conveniently lie in the range of from 0° C. to the boiling point of the reaction mixture, e.g. at about ambient temperature. Inert solvents may be used where desired.

Examples of suitable bases include alkaline metal hydroxides such as sodium hydroxide, alkaline metal hydrides such as sodium hydride, alkaline metal alcoholates such as sodium methylate, alkaline metal carbonates or alkaline metal hydrogen carbonate such as potassium carbonate or sodium hydrogen carbonate.

Examples of suitable inert solvents include aromatic hydrocarbons such as benzene and toluene; ethers such as diethyl ether, tetrahydrofuran and 1,2-dimethoxyethane; polar solvents such as dimethylformamide, dimethyl sulfoxide, water, alcohols such as methanol; acetone or a mixture comprising two or more of them.

The desired end-product is isolated and purified according to known techniques, for example by evaporation of solvent, chromatography and crystallisation. The compounds of formula I are basic in nature. They may form salts with sufficiently strong acids such as HCl and HBr.

The compounds of formula II wherein A is CH may be obtained by reaction of compounds of formula III

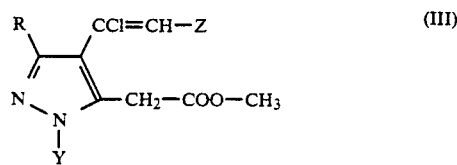

wherein R, Y and Z are as defined above with methyl formate in the presence of a base.

This reaction is essentially a Claisen reaction and may be carried out under the conditions known for such reaction.

The compounds of formula II wherein A is N may be obtained by reaction of compounds of formula III with a lower alkyl nitrite in the presence of a base. Alkyl nitriles are according to this invention preferably selected from $C_1$-$C_5$alkyl nitrites. Examples for suitable nitriles are iso-amyl nitrite or tert.butyl nitrite.

The reaction (III→II) may be carried out in an inert solvent.

Examples of suitable solvents are as described for the O-methylation of the compounds of formula (II).

Examples of suitable bases are such typically used for a Claisen reaction such as alkaline metal alcoholates, e.g. sodium methylate and alkaline metal hydrides e.g. sodium hydride.

The reaction temperature may vary within wide ranges, e.g. from 0° C. to the boiling point of the reaction mixture and is preferably at or near ambient temperature.

The acetic acid esters of formula III may be obtained from compounds of formula IV

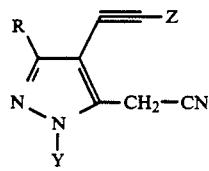

wherein R, Y and Z are as defined above by alcoholysis with HCl in the presence of methanol.

Compounds of formula IV may be obtained in a manner known per se from known compounds, e.g. analogous to the processes described in the examples hereinafter.

For example compounds of formula IV wherein R is $CF_3$ may be obtained by treating a compound of formula V

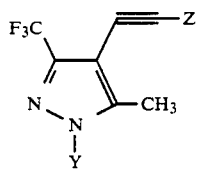

with a metallation reagent such as n-butyllithium, and quenching the intermediate with $CO_2$ and esterifying the free acid function with methanol.

The compounds of formula (I) are effective against phytopathogens.

Their advantageous fungicidal activity is established by in vivo tests with test concentrations from 0.5 to 500 mg a.i./l against Uromyces appendiculatus on pole beans, against Puccinia triticina on wheat, against Sphaerotheca fuliginea on cucumber, against Erysiphe graminis on wheat and barley, against Podosphaera leucotricha on apple, against Uncinula necator on grape vine, against Leptosphaeria nodorum on wheat, against Cochliobolus sativus and Pyrenophora graminea on barley, against Venturia inaequalis on apple, against Phytophthora infestans on tomato and against Plasmopara viticola on grape vine.

Many of the compounds of formula (I) have an excellent plant tolerance and a systemic action. The compounds of the invention are therefore indicated for treatment of plant, seeds and soil to combat phytopathogenic fungi, e.g. Basidiomycetes of the order Uredinales (rusts) such as Puccinia spp, Hemileia spp, Uromyces spp; and Ascomycetes of the order Erysiphales (powdery mildew) such as Erysiphe ssp, Podosphaera spp, Uncinula spp, Sphaerotheca spp; as well as Cochliobolus; Pyrenophora spp; Venturia spp; Mycosphaerella spp; Leptosphaeria; Deuteromycetes such as Pyricularia, Pellicularia (Corticium), Botrytis; and Oomycetes such as Phytophthora spp, Plasmopara spp.

The compounds of formula (I) are particularly effective against powdery mildew and rust fungi, in particular against pathogens of monocotyledoneous plants such as cereals, including wheat.

The amount of compound of the invention to be applied, will depend on various factors such as the compound employed, the subject of the treatment (plant, soil, seed), the type of treatment (e.g. spraying, dusting, seed dressing), the purpose of the treatment (prophylactic or therapeutic), the type of fungi to be treated and the application time.

In general, satisfactory results are obtained, if the compounds of the invention are applied in an amount of from about 0.0005 to 2.0, preferably about 0.01 to 1 kg/ha, in the case of a plant or soil treatment; e.g. 0.04 to 0.500 kg of active ingredient (a.i.) per ha in field crops such as cereals, or concentrations of 4 to 50 g of a.i. per hl in crops such as fruits, vineyards and vegetables (at an application volume of from 300 to 1000 l/ha—depending on the size or leaf volume of the crop—which is equivalent to an application rate of approximately 30–500 g/ha). The treatment can, if desired, be repeated, e.g. at intervals of 8 to 30 days.

Where the compounds of the invention are used for seed treatment, satisfactory results are in general obtained, if the compounds are used in an amount of from about 0.05 to 0.5, preferably about 0.1 to 0.3 g/kg seeds.

The term soil as used herein is intended to embrace any conventional growing medium, whether natural or artificial.

The compounds of the invention may be used in a great number of crops, such as soybean, coffee, ornamentals (i.a. pelargonium, roses), vegetables (e.g. peas, cucumber, celery, tomato and bean plants), sugarbeet, sugarcane, cotton, flax, maize (corn), vineyards, pomes and stone fruits (e.g. apple, pears, prunes) and in cereals (e.g. wheat, oats, barley, rice).

Preferred compounds of formula I have one, preferably more, more preferably all of the following features
R is $CF_3$ or $CH_3$;
Y is $CH_3$ and
Z is phenyl, unsubstituted or mono- or di-substituted by substituents selected from halogen, $C_{1-4}$alkyl, $C_{1-4}$alkoxy and $CF_3$; or is $C_{1-6}$alkyl or thienyl.

The invention also provides fungicidal compositions, comprising as a fungicide a compound of formula I in association with a agriculturally acceptable diluent (hereinafter diluent). They are obtained in conventional manner, e.g. by mixing a compound of the invention with a diluent and optionally additional ingredients, such as surfactants.

The term diluents as used herein means liquid or solid agriculturally acceptable material, which may be added to the active agent to bring it in an easier or better applicable form, resp. to dilute the active agent to a usable or desirable strength of activity. Examples of such diluents are talc, kaolin, diatomaceous earth, xylene or water.

Especially formulations used in spray form, such as water dispersible concentrates or wettable powders, may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent, from 0 to 20% agriculturally acceptable surfactant and from 10 to 99.9% diluent(s). Concentrated forms of composition, e.g. emulsion concentrates, contain in general from about 2 to 90%, preferably from between 5 and 70% by weight of active agent. Application forms of formulation contain in general from 0.0005 to 10% by weight of a compound of the invention as active agent typical spray-suspensions may, for example, contain from 0.0005 to 0.05, e.g. 0.0001, 0.002 or 0.005% by weight of active agent.

In addition to the usual diluents and surfactants, the compositions of the invention may comprise further additives with special purposes, e.g. stabilisers, desactivators (for solid formulations or carriers with an active surface), agents for improving the adhesion to plants, corrosion inhibitors, anti-foaming agents and colorants. Moreover, further fungicides with similar or complementary fungicidal activity, e.g. sulphur, chlorothalonil, euparen; a guanidine fungicide such as guazatine; dithiocarbamates such as mancozeb, maneb, zineb, propineb; trichloromethane sulphenylphthalimides and analogues such as captan, captafol and folpet; benzimidazoles such as carbendazim, benomyl; azoles such as cyproconazole, flusilazole, flutriafol, hexaconazole propiconazole, tebuconazole, prochloraz; morpholines such as fenpropimorph, fenpropidine, or other beneficially-acting materials, such as cymoxanil, oxadixyl, metalaxyl, or insecticides may be present in the formulations.

Examples of plant fungicide formulations are as follows:

a. Wettable Powder Formulation

10 Parts of a compound of formula I are mixed and milled with 4 parts of synthetic fine silica, 3 parts of sodium lauryl sulphate, 7 parts of sodium lignin sulphonate and 66 parts of finely divided kaolin and 10 parts of diatomaceous earth until the mean particle size is about 5 micron. The resulting wettable powder is diluted with water before use to a spray liquor which may be applied by foliar spray as well as by root drench application.

b. Granules

Onto 94.5 parts by weight of quartz sand in a tumbler mixer are sprayed 0.5 parts by weight of a binder (non-ionic tenside) and the whole thoroughly mixed. 5 parts by weight of a compound of formula I invention are then added and thorough mixing continued to obtain a granulate formulation with a particle size in the range of from 0.3 to 0.7 mm (where required, the granules may be dried by the addition of 1 to 5% by weight of talcum). The granules may be applied by incorporation into the soil adjacent to the plants to be treated.

c. Emulsion Concentrate

10 Parts by weight of a compound of formula I are mixed with 10 parts of weight of an emulsifier and 80 parts by weight of xylene. The thus obtained concentrate is diluted with water to form an emulsion of the desired concentration, prior to application.

d. Seed Dressing

45 Parts of a compound of formula I are mixed with 1.5 parts of diamyl phenoldecaglycolether ethylene oxide adduct, 2 parts of spindle oil, 51 parts of fine talcum and 0.5 parts of colorant rhodanin B. The mixture is ground in a contraplex mill at 10,000 rpm until an average particle size of less than 20 microns is obtained. The resulting dry powder has good adherence and may be applied to seeds, e.g. by mixing for 2 to 5 minutes in a slowly turning vessel.

The following examples further illustrate the present invention. All temperatures are in centigrade. Rf values are obtained by thin layer chromatography on silica gel, unless otherwise specified.

EXAMPLE 1

Methyl α-[1-methyl-4-phenylethinyl-5-pyrazol]-β-methoxacrylate

To methyl α-[1-methyl-4-phenylethinyl-5-pyrazol]-β-hydroxypropenoate (52 g) in dimethylformamide (200 ml) are added $K_2CO_3$ (50 g, 0.36 mol) and methyliodide (51 g, 0.36 mol), and the mixture is stirred for 3 hours at +25° C. The reaction mixture is diluted with ether and filtered. The filtrate is washed with brine, dried over $MgSO_4$, filtered and concentrated under reduced pressure. The thus obtained 12:1 E/Z mixture of the title compound is chromatographed over silica gel (eluent: hexane/ethyl acetate 1:1) to give the individual E and Z isomers. The E-isomer is obtained as an oil; the Z-isomer has a m.p. of 70°-72° C.

$^1$H-NMR (CDCl$_3$): E: 7.74 (s, 1H); 7.63 (s, 1H); 7.45-7.25 (m, 5H); 3.93 (s, 3H); 3.73 (s, 3H); 3.70 (s, 3H). Z: 7.63 (s, 1H); 7.45-7.25 (m, 5H); 6.96 (s, 1H); 4.02 (s, 3H); 3.77 (s, 3H); 3.73 (s, 3H).

EXAMPLE 2

Methyl α-[1,3-dimethyl-4-phenylethinyl]-5-pyrazol]-β-methoxyacrylate

Following the procedure of Example 1 the E and Z isomers of the title compound are obtained starting from the corresponding β-hydroxypropenoate. The E-isomer has a m.p. of 103°-105° C.; the Z-isomer has a m.p. of 109°-110° C.

$^1$H-NMR (CDCl$_3$): E: 7.73 (s, 1H); 7.45-7.25 (m, 5H); 3.96 (s, 3H); 3.75 (s, 3H); 3.66 (s, 3H); 2.35 (S, 3H) Z: 7.45-7.25 (m, 5H); 6.94 (s, 1H); 4.00 (s, 3H); 3.77 (s, 3H); 3.73 (s, 3H).

EXAMPLE 3

Methyl α-[1-methyl-3-trifluoromethyl-4-(4-fluorophenylethinyl)-5-pyrazol]-α-methoximino acetate 0.9 g of a 80% suspension of NaH (0.03 mol) is solved in a mixture of 30 ml of 1,2-dimethoxyethane and 1 ml of methanol at +20° C. To this mixture a solution of 3.0 g (0.01 mol) of methyl α-[methyl-3-trifluoromethyl-4-(4-fluorophenylethinyl)-5-pyrazol]-acetate in 2.7 ml (0.02 mol) of iso-amyl nitrite is added dropwise. After 15 minutes 5 ml of methyl iodide are added. The reaction mixture is agitated for 1 hour at +25° C., then diluted with diethyl ether and washed with brine. The organic phase is separated, dried with $MgSO_4$ and concentrated. The residue is chromatographed over silica gel (eluent: hexane/ethyl acetate 1:1), yielding pure methyl α-[1-methyl-3-trifluoromethyl-4-(4-fluorophenylethinyl)-5-pyrazol]-α-methoxyimino acetate in form of colourless crystals, m.p. 101°-103° C.

$^1$H-NMR (CDCl$_3$): 7.46-6.98(m, 4H, arom.); 4.20 (s, 3H, OCH$_3$); 3.92 (s, 3H, OCH$_3$); 3.81 (s, 3H, NCH$_3$)

Intermediates

EXAMPLE 4

Methyl α-(1-methyl-4-phenylethinyl-pyrazolyl)-β-hydroxypropenoate

Methyl α-[1-methyl-4-(1-phenyl-2-chloro-2-ethenyl)-5-pyrazolyl]-acetate (80 g, 0.28 mol) are dissolved in methyl formate (300 ml) and added to a suspension of NaH (30 g, 80% in oil, 1 mol) in 1,2-dimethoxyethane (800 ml) and methanol (1 ml), such that the reaction temperature does not exceed +30° C. After 16 hours, the mixture is poured onto ice and the organic solvents sucked off under reduced pressure. The aqueous phase is washed with diethylether and subsequently acidified with dilute hydrochloric acid. The title compound is extracted with diethyl ether and concentrated and used as such in Example 1.

EXAMPLE 5

Methyl α-[1,3-dimethyl-4-phenylethinyl-5-pyrazolyl]-β-hydroxypropenoate

Following the procedure of Example 4, methyl α-(1,3-methyl-4-phenylethinyl-5-pyrazolyl)-β-hydroxypropenoate is obtained from methyl α-[1,3-methyl-4-(1-phenyl-2-chloro-2-ethenyl)-5-pyrazolyl]-acetate.

EXAMPLE 6

Methyl α-[1-methyl-4-(1-phenyl-2-chloro-2-ethenyl)-5-pyrazolyl]acetate a) 1-Methyl-4-phenylethinylpyrazole To a solution of 1-methyl-4-iodopyrazole (208 g, 1 mol) and phenylacetylene (112 g, 1.1 mol) in diisopropylamine (2 l) are added, under nitrogen, copperiodide (2 g), triphenylphosphine (0.1 g) and bis-(triphenylphosphine) palladiumdichloride (0.5 g). The mixture is kept during 3 hours at ca. +35° C. and then heated for 1 hour at +90° C. The cooled reaction mixture is diluted with ethyl acetate and filtrated. Concentration of the filtrate and distillation yields the title compound: b.p. 116°–118° C./0.3 mbar, m.p. 70°–72° C.

b) 5-Formyl-1-methyl-4-phenylethinylpyrazole

To a solution of the compound of Example 6a (100 g, 0.55 mol) in absolute tetrahydrofuran (600 ml) is added, dropwise, at −50° C., n-butyllithium (400 ml, 1.6M in hexane). To the suspension of the lithium salt is added, after 30 minutes, dimethylformamide (100 ml), such that the temperature does not exceed −40° C. After further 30 minutes, the clear solution is poured onto diluted hydrochloric acid and the organic solvents sucked off under reduced pressure. The crystals are filtered off and dried (m.p. 90°–91° C.).

c) 5-Hydroxymethyl-1-methyl-4-phenylethinylpyrazole

The aldehyde of Example 6b) (100 g, 0.48 mol) is, in 10 portions, added to a cooled solution of sodium dihydro-bis-(2-methoxyethoxy) aluminate (75 ml, 3.5M in toluene, 0.25 mol) in 1,2-dimethoxyethane 250 ml). After 30 minutes the mixture is carefully poured onto cold dilute hydrochloric acid. The product is filtered off and dried (m.p. 143°–145° C.).

d) 5-Chloromethyl-1-methyl-4-phenylethinylpyrazole

To a suspension of the alcohol of Example 6c) (100 g, 0.48 mol) in dichloromethane (1 L) is added dropwise, at room temperature thionyl chloride (30 ml, 0.5 mol). After 10 hours the reaction mixture is rendered alkaline with aqueous sodium carbonate. The product is obtained as an oil.

$^1$H-NMR(CDCl$_3$): 7.62 (s, 1H, pyrazole); 7.55–7.32 (m, 5H, arom); 4.95 (s, 2H, CH$_2$); 3.96 (s,, 3H, NMe).

e) (1-Methyl-4-phenylethinyl-5-pyrazolyl)acetonitrile

A solution of the compound of Example 6d) (104 g, 0.46 mol) in acetonitrile (200 ml) is added, at +80° C., dropwise, within 60 minutes to a suspension of KCN (55 g, 0.86 mol) and 18.6 Crownether (5 g) in acetonitrile. After further 60 minutes, the reaction mixture is cooled, diluted with ether and washed with brine. The thus obtained nitrile has, after chromatography over silica gel (hexane/ethyl acetate 2:1) a m.p. of 95°–96° C. (colourless crystals).

f) Methyl α-[1-methyl-4-(1-phenyl-2-chloro-2-ethenyl) 5-pyrazolyl]acetate

The acetonitrile (73 g, 0.33 mol) is dissolved in methanol (700 ml) and the solution saturated, at room temperature, with hydrochloric acid. After 2 hours reflux, the major amount of solvent is sucked off under reduced pressure. The residue is rendered alkaline with aqueous Na$_2$CO$_3$ and extracted with diethylether. The organic phase is dried (MgSO$_4$), filtered and concentrated. It is employed without further purification in the process of Example 4.

$^1$H-NMR (CDCl$_3$): 7.44 (s, 1H, pyrazole); 7.24–7.05 (m, 5H, arom); 6.91 (s, $^1$H, vinyl); 3.83 (s, 3H, OMe); 3.57 (s, 2H, CH$_2$); 3.52 (s, 3H, NMe).

EXAMPLE 7

Methyl α-[1,3-dimethyl-4-(1-phenyl-2-chloro-2-ethenyl)-5-pyrazolyl]acetate a) 1,3-Dimethyl-4-iodo-5-pyrazolcarboxylic acid ethyl ester 1,3-Dimethyl-5-pyrazolcarboxylic acid ethyl ester (185 g, 1.1 mol), iodine (140 g, 0.55 mol) and HIO$_3$ (38.7 g, 0.22 mol) are heated, under reflux, in acetic acid glacial (450 ml), water (150 ml) and 1,2-dichloroethane (150 ml) for 1.5 hours. The mixture is discoloured with saturated sodium bisulfite, evaporated under reduced pressure and the product extracted with ether. The organic phase is washed with sodium bisulfite and aqueous sodium bicarbonate solution.

The organic phase is dried (MgSO$_4$), filtered and concentrated to give the title compound m.p. 31°–34° C.

b) 1,3-Dimethyl-4-phenylethinyl-5-pyrazolecarboxylic acid ethyl ester

Reaction of the compound of Example 7a) with phenylacetylene analogous to the process of Example 6a yields this compound having a m.p. of 97°–98° C.

c) 1,3-Dimethyl-5-hydroxymethyl-4-phenylethinyl pyrazole

Reaction of the compound of Example 7b) under conditions analogous to those of Example 6c, yields the alcohol (m.p. 120–121)

d) 5-Chloromethyl-1,3-dimethyl-4-phenylethinyl pyrazole

Reaction of the compound of Example 7c) under conditions analogous to those of Example 6d yields the chloride of m.p. 74°–77° C. (colourless crystals).

e) (1,3-Dimethyl-4-phenylethinyl-5-pyrazolyl) acetonitrile

Reaction of the compound of Example 7d, under conditions analogous to those of Ex. 6e yields the nitrile, m.p. 105°–106° C.

f) Methyl α-[1,3-dimethyl-4-(1-phenyl-2-chloro-2-ethenyl)-5-pyrazolyl]acetate

Reaction of the compound of Example 7e) under conditions analogous to those of Example 6f yields the title compound.

$^1$H-NMR (CDCl$_3$): 7.24–7.01 (m, 5H, arom); 6.97 (s, 1H, vinyl); 3.78 (s, 3H, OMe); 3.62 (s, 2H, CH$_2$); 3.55 (s, 3H, NMe).

EXAMPLE 8:

Methyl α-[1-methyl-3-trifluoromethyl-4-(4-fluorophenylethinyl)-5-pyrazol]-acetate a) 1,5-Dimethyl-3-trifluoromethylpyrazole 486 ml (3.5 mol) of trifluoroacetic acid anhydride are added dropwise to a solution of 330 ml (3.5 mol) isopropenyl-methylether in a mixture of 600 ml of tert.butyl-methylether and 290 ml (3.5 mol) of pyridine at a temperature of 0° C. to +5° C. After a reaction period of 30 minutes at +5° C. the mixture is washed with 1 L of water and 0.5 L of saturated sodium bicarbonate solution. The organic phase is separated and at −20° C. and 180 ml of methylhydrazine are added dropwise. The mixture is allowed to warm up to room temperature, and it is dried with MgSO$_4$ and concentrated under reduced pressure. The residue is distilled, b.p. +70° C. (21 mbar) yielding 498 g of 1,5-dimethyl-3-trifluoromethylpyrazole.

b) 1,5-Dimethyl-3-trifluoromethyl-4-iodopyrazole

Reaction of the compound of Example 8a) under conditions analogous to Example 7a yields this compound having a m.p. 98°-100° C.

c) 1,5-Dimethyl-3-trifluoromethyl-4-(4-fluorophenylethinyl)-pyrazole

Reaction of the compound of Example 8b) with 4-fluorophenylacetylane analogous to the process of Example 6a yields this compound having a m.p. 61°-62° C., b.p. 135°-140° C. (0.05 mbar).

d) 94 ml (0.15 mol) of a 1.6 molar solution of n-butyllithium in hexane is added dropwise at −50° C. to a solution of 35 g (0.12 mol) of the compound of 8c) in 200 ml of tetrahydrofuran. The obtained red solution is poured onto ground solid CO$_2$. The organic solvent is evaporated and the residue is taken up with water, acidified with 20% hydrochloric acid extracted with diethyl ether. The organic phase is dried with MgSO$_4$ and concentrated. The oily residue (approx. 35 g) is solved in methanol and mixed with 18 ml (0.25 mol) of thionyl chloride at 0° C. After a reaction period of 3 hours, the mixture is concentrated under reduced pressure and 35 g of crude methyl α-[1-methyl-3-trifluoromethyl-4-(4-fluorophenylethinyl)-5-pyrazol]-acetate are obtained.

The compounds of the following tables are obtained in analogous manner:

TABLE 1

Compounds of formula I, wherein A is CH and Y is CH$_3$

| Comp No. | R | Z | physical data |
|---|---|---|---|
| 1.01 | H | phenyl | E: oil |
| 1.02 | H | phenyl | Z: m.p. 70–72° C. |
| 1.03 | CH$_3$ | phenyl | E: m.p. 103–105° C. |
| 1.04 | CH$_3$ | phenyl | Z: m.p. 109–110° C. |
| 1.05 | CH$_3$ | 4-chlorophenyl | E: m.p. 113–114° C. |
| 1.06 | CH$_3$ | 4-fluorophenyl | E: m.p. 109–110° C. |
| 1.07 | CH$_3$ | 4-methoxyphenyl | E: m.p. 121–122° C. |
| 1.08 | CH$_3$ | 4-methylphenyl | E: m.p. 104–105° C. |
| 1.09 | CH$_3$ | n-hexyl | E: oil |
| 1.10 | CH$_3$ | 3-CF$_3$-phenyl | E: m.p. 85–86° C. |
| 1.11 | CH$_3$ | 3,4-dichlorophenyl | E: m.p. 79–80° C. |
| 1.12 | tert.butyl | phenyl | E: m.p. 143° C. |
| 1.13 | CH$_3$ | 3-chloro-4-methoxyphenyl | E: m.p. 124–126° C. |
| 1.14 | CF$_3$ | 4-chlorophenyl | E: m.p. 74–77° C. |
| 1.15 | CF$_3$ | 4-fluorophenyl | E: m.p. 93–95° C. |
| 1.16 | CF$_3$ | 3-chloro-4-methylphenyl | E: m.p. 120° C. |
| 1.17 | CF$_3$ | β-naphthyl | E: m.p. 115° C. |
| 1.18 | CF$_3$ | 2,5-dichlorophenyl | E: m.p. 90–92° C. |
| 1.19 | CH$_3$ | 2,3-dichlorophenyl | |
| 1.20 | CF$_3$ | 2,3-dichlorophenyl | |
| 1.21 | CH$_3$ | 2,4-dichlorophenyl | |
| 1.22 | CF$_3$ | 2,4-dichlorophenyl | |
| 1.23 | CH$_3$ | 3-chlorophenyl | |
| 1.24 | CF$_3$ | 3-chlorophenyl | |
| 1.25 | CH$_3$ | 3-fluorophenyl | |
| 1.26 | CF$_3$ | 3-fluorophenyl | |
| 1.27 | CH$_3$ | 1-methyl-1-(4-chlorophenyl)-ethyl | |
| 1.28 | CF$_3$ | 1-methyl-1-(4-chlorophenyl)-ethyl | |
| 1.29 | CH$_3$ | 3-chlorobenzyl | |
| 1.30 | CF$_3$ | 3-chlorobenzyl | |
| 1.31 | CH$_3$ | phenethyl | |
| 1.32 | CF$_3$ | phenethyl | |
| 1.33 | CH$_3$ | 1-methyl-1-(3-chlorophenyl)-ethyl | |
| 1.34 | CF$_3$ | 1-methyl-1-(3-chlorophenyl)-ethyl | |
| 1.35 | CH$_3$ | 1-methyl-1-(3-CF$_3$-phenyl)-ethyl | |
| 1.36 | CF$_3$ | 1-methyl-1-(3-CF$_3$-phenyl)-ethyl | |

TABLE 2

Compounds of formula I wherein A is N and Y is CH$_3$

| Comp. No. | R | Z | physical data |
|---|---|---|---|
| 2.01 | CF$_3$ | phenyl | m.p. 90–93° C. |
| 2.02 | CF$_3$ | 4-fluorophenyl | m.p. 101–103° C. |
| 2.03 | CH$_3$ | 3-CF$_3$-phenyl | |
| 2.04 | CH$_3$ | 4-fluorophenyl | |
| 2.05 | CH$_3$ | 3-chloro-4-methoxyphenyl | |
| 2.06 | CF$_3$ | 3-CF$_3$-phenyl | |
| 2.07 | CH$_3$ | phenyl | |
| 2.08 | CH$_3$ | 3-fluorophenyl | |
| 2.09 | CF$_3$ | 3-fluorophenyl | |
| 2.10 | CH$_3$ | 3-chlorophenyl | |
| 2.11 | CF$_3$ | 3-chlorophenyl | |
| 2.12 | CH$_3$ | 2,3-dichlorophenyl | |
| 2.13 | CF$_3$ | 2,3-dichlorophenyl | |

EXAMPLE A

Activity against Powdery Mildew

*Sphaerotheca fuliginea:*

Plants of *Cucumis sativus* (cucumber), 7 days old (cotyledon stage), are sprayed to near run off with a suspension containing 100 mg/l of active ingredient. The deposit is then allowed to dry. One day later, the treated plants are inoculated with a spore suspension containing $1\times10^5$/ml of freshly collected conidia of *Sphaerotheca fuliginea* and then incubated in the greenhouse for 7 days at +24° C. and 60% r.h.

The efficacy of the test compounds is determined by comparing the degree of fungal attack with that on untreated, similarly inoculated check plants. In this test compounds 1.05, 1.06, 1.10, 1.13 and 2.02 showed an efficacy of more than 90%.

Similar methods are used to test the compounds against the following pathogens:
*Podosphaera leucotricha* on apple
*Erysiphe graminis* on wheat and barley (dry inoculation)
*Uncinula necator* on grape

EXAMPLE B

Activity against Rust, Scab, Pyrenophora, Leptosphaeria

*Uromyces appendiculatus:*

Plants of *Phaseolus vulgaris* (pole bean), 14 days old (2 leaves stage), are sprayed to near run off with a suspension containing 100 mg/l of the active ingredient. The deposit is then allowed to dry. One day later, the treated plants are inoculated with a spore suspension containing $1\times10^5$/ml of freshly collected spores of *Uromyces appendiculatus*. Incubation is performed for 3 days in a high humidity cabinet at +23° C. and >95% r.h. and thereafter during 10 days at +24° C. and 60% r.h.

The efficacy the compounds is determined by comparing the degree of fungal attack with that on untreated, similarly inoculated check plants. In this test compounds 1.05, 1.06, 1.10, 1.13 and 2.02 showed an efficacy of at least 90%.

Similar methods are used to test the compounds against the following pathogens:
*Puccinia triticina* on wheat (plants 10 days old)
*Pyrenophora graminea* on barley
*Leptosphaeria nodorum* on wheat
*Venturia inaequalis* on apple (plants 21 days old; the spore suspension contains 1% malt)

EXAMPLE C

Activity Against Downy Mildew

Plants of *Lycopersicon esculentum* (tomato) with 6 leaves, are sprayed to near run off with a spray suspension containing 500 mg/l of the active ingredient. The deposit is then allowed to dry. 1 day later, the treated plants are inoculated with a spore suspension containing $1\times10^5$/ml of freshly collected sporangia of *Phytophthora infestans* and then incubated for 7 days in a high humidity cabinet at +18° C. and >95% r.h. The efficacy of the test compounds is determined by comparing the degree of fungal attack with that on untreated, similarly inoculated check plants.

A similar method is used to test the compounds against *Plasmopara viticola* on grape vine.

EXAMPLE D

Activity after seed treatment

The compounds of the invention may also be used for seed treatment. The advantageous fungicidal activity is established by in vitro tests with the following pathogens:
*Pyrenophora graminea*
*Ustilago nuda*
*Gerlachia nivalis*
*Leptoshpaeria nodorum*

Autoclaved wheat seeds are inoculated with spores or mycelium of the pathogens and coated with different concentrations of the test compounds resulting in dosages of 50 g a.i./100 kg seed. The treated seeds are then placed on agar plates and the pathogens allowed to grow for 3-8 days at +24° C. in the dark.

The efficacy of the test compounds is determined by comparing the degree of fungal growth emerging from treated and untreated inoculated seeds.

To evaluate the plant tolerance of the compounds, healthy seeds of wheat and barley are coated with the dosages mentioned above. The seeds are then allowed to germinate in petri dishes on moist filter paper in high humidity at +18° C. for 10 days. Plant damage is recorded, comparing the growth of treated and untreated seedlings.

In this test compounds 1.05, 1.06 and 1.10 showed an efficacy of at least 90% against *Pyrenophora graminea*.

We claim:

1. Compounds of formula I

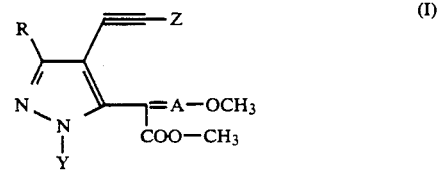

wherein
R is H, $C_{1-4}$alkyl; optionally substituted aryl or $CF_3$;
Y is $C_{1-4}$alkyl or optionally substituted aryl;
A is nitrogen or CH; and
Z is optionally substituted hydrocarbyl or optionally substituted heteroaryl.

2. Compounds according to claim 1, wherein
R is H, $C_{1-4}$alkyl, phenyl or phenyl mono- or disubstituted by substituents selected from $C_{1-4}$alkyl, $C_{1-4}$alkoxy, $C_{1-4}$haloalkyl, $C_{1-4}$haloalkoxy and halogen;
Y is $C_{1-4}$alkyl, phenyl or phenyl mono- or disubstituted by substituents selected from $C_{1-4}$alkyl, $C_{1-4}$alkoxy, $C_{1-4}$haloalkyl, $C_{1-4}$haloalkoxy and halogen;
Z is either thienyl, group G1 or G2,

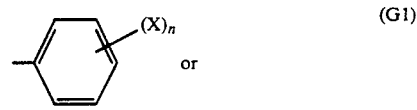

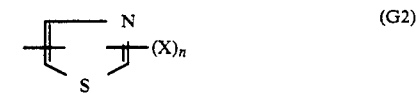

wherein X is independently hydrogen; halogen; cyano; nitro; $C_1$-$C_4$alkyl, $C_2$-$C_3$alkenyl, $C_1$-$C_3$alkoxy, $C_2$-$C_3$alkenyloxy, $C_2$-$C_3$alkynyloxy each optionally substituted with one or more substituents selected from halogen and trifluoromethyl; or phenyl, phenoxy, benzyl, benzyloxy, thiazolyl, thiazolyloxy, pyridyloxy or benzothiazolyloxy, each optionally substituted with one or more substituents selected from halogen, trifluoromethyl, $C_1$-$C_4$ alkyl and $C_1$-$C_4$ alkoxy; m is 1 or 2; and n is a integer of 1–5; or two Xs may form a fused ring together with the benzene ring to which they are attached, where the fused ring is selected from 2,3-dihydrobenzofuran, chroman, naphtalene, fluorene, anthraquinone or benzo-1,3-dioxolane; or Z is $C_{1-4}$haloalkyl or phenoxy-$C_{1-4}$alkyl unsubstituted mono- or disubstituted in the phenyl moiety by substituents selected from $C_{1-4}$alkyl, $C_{1-4}$alkoxy, $C_{1-4}$haloalkyl, $C_{1-4}$haloalkenyl and halogen; or Z is phenyl-$C_{1-4}$alkyl unsubstituted or monosubstituted in the alkyl moiety by OH or $C_{1-4}$alkoxy, and/or mono- or disubstituted in the phenyl moiety by X, wherein X is as defined in this claim.

3. A compound according to claim 2, wherein X independently is hydrogen, halogen, $C_{1-4}$alkyl, $C_{1-4}$alkoxy, $CF_3$, $CF_3O$, phenyl or phenoxy.

4. A compound according to claim 2, wherein Z is selected from chlorophenyl, fluorophenyl, methoxyphenyl, methylphenyl, trifluoromethylphenyl, dichlorophenyl, chloro-methoxyphenyl, and chloro-methylphenyl.

5. A compound according to claim 1, wherein R is $CF_3$ or $CH_3$; Y is $CH_3$; and Z is phenyl, $C_1$-$C_6$-alkyl, thienyl, phenyl or phenyl which is mono- or di-substituted by substituents selected from halogen, $C_{1-4}$alkyl, $C_{1-4}$alkoxy and $CF_3$.

6. A compound according to claim 1, selected from the group comprising methyl α-[1,3-dimethyl-4-(4-fluorophenylethinyl)-5-pyrazol]-β-methoxyacrylate; methyl α-[1,3-dimethyl-4-(3-trifluoromethylphenylethinyl)-5-pyrzol]-β-methoxyacrylate; methyl α-[1,3-dimethyl-4-(3-chloro-4-methoxyphenylethinyl)-5-pyrazol]-β-methoxyacrylate, and methyl α-[1-methyl-3-trifluoromethyl-4-(4-chlorophenylethinyl)-5-pyrazol]-β-methoxyacrylate.

7. Method of combatting phytopathogenic fungi comprising applying to the fungi or their habitat a fungicidally effective amount of the compound of formula I according to claim 1.

8. Fungicidal composition comprising a compound of formula I stated in claim 1 and a agriculturally acceptable diluent.

* * * * *